US006776987B1

(12) United States Patent
Edelberg et al.

(10) Patent No.: US 6,776,987 B1
(45) Date of Patent: Aug. 17, 2004

(54) ENHANCEMENT OF CARDIAC CHRONOTROPY

(75) Inventors: Jay M. Edelberg, New York, NY (US); Robert D. Rosenberg, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/614,326

(22) Filed: Jul. 12, 2000

Related U.S. Application Data

(63) Continuation of application No. PCT/US99/00732, filed on Jan. 13, 1999.
(60) Provisional application No. 60/071,456, filed on Jan. 13, 1998.

(51) Int. Cl.[7] .................. A01N 63/00; A01N 65/00; A01N 43/04; A61K 48/00; A61K 31/70
(52) U.S. Cl. ................. 424/93.21; 424/93.1; 424/93.2; 514/44
(58) Field of Search ................... 424/93.21, 93.2, 424/93.1; 514/44; 800/3, 18, 8, 9, 11, 13; 435/325

(56) References Cited

FOREIGN PATENT DOCUMENTS

| WO | WO 90/10471 | 9/1990 |
| WO | WO 97/17937 | 5/1997 |

OTHER PUBLICATIONS

Strauer and Komowski. Circulation (2003) 107:929–934.*
Murray et al. Journal of Cardiac Failure (2002) 8:S532–S541.*
Muller–Elmsen et al. Congest. Heart Fail. (2002) 8:220–227.*
Barnett, J. et al., "Effects of Low–Density Lipoproteins and Mevinolin on Sympathetic Responsiveness in Cultured Chick Atrial Cells.", *J. Biol. Chem., 264*:10779–86 (1989).
Beau, S. et al., "Relative Densities of Muscarinic Cholinergic and β–Adrenergic Receptors in the Canine Sinoatrial Node and Their Relation to Sites of Pacemaker Activity.", *Circ. Res., 77*:957–963 (1995).
Bertin, B. et al., "Specific atrial overexpression of G protein coupled human $\beta_1$ adrenoceptors in transgenic mice.", *Cardiovasc. Res., 27*:1606–12 (1993).
Brodde, O., "β–Adrenergic receptors in failing human myocardium.", *Basic Res. Cardiol., 91 Suppl. 2*:35–40 (1996).
Brown, A., "Regulation of heartbeat by G protein–coupled ion channels.", *Am. J. Physiol., 259*:H1621–H1628 (1990).
Chung, F. et al., "Cloning and sequence analysis of the human brain β–adrenergic receptor: Evolutionary relationship to rodent and avian β–receptors and porcine muscarinic receptors.", *FEBS Lett,. 211*:200–206 (1987).
Crisp, T., "Adrenergic Drugs.", *Bas. Pharm. Med.,* Chapter 8: 113–29.

DiFrancesco, D., "Characterization of single pacemaker channels in cardiac sino–atrial node cells.", *Nature, 324*:470–3 (1986).
Drazner, M. et al., "Potentiation of β–Adrenergic Signaling by Adenoviral–mediated Gene Transfer in Adult Rabbit Ventricular Myocytes.",*J. Clinic. Invest., 99*:288–96 (1997).
Drazner, M. et al., "Potentiation of β–Adrenergic Signaling by Gene Transfer.", *Proc. Assoc. Am. Physicians, 109*:220–227 (1997).
Ellison, K. et al., "Fusigenic Liposome–mediated DNA Transfer into Cardiac Myocytes.", *J. Mol. Cell. Cardiol., 28*:1385–1399 (1996).
Field, L., "Atrial natriuretic factor–SV40 T antigen transgenes produce tumors and cardiac arrhythmias in mice.", *Science, 239*:1029–33 (1988).
Fulmer, R. et al., "Transplantation of Cardiac Tissue into the Mouse Ear.", *Am. J. Anat., 113*:273–286 (1963).
Gal, D. et al., "Direct Myocardial Transfection in Two Animal Models.", *Lab. Invest., 68*:18–25 (1993).
Gerhardt, M. et al., "Acute Myocardial β–Adrenergic Receptor Dysfunction After Cardiopulmonary Bypass in Patients with Cardiac Valve Disease.", *Circulation 98*: II 275–281 (1998).
Giordano, F. et al., "Intracoronary gene transfer of fibroblast growth factor–5 increases blood flow and contractile function in an ischemic region of the heart.", *Nat. Med. 2*:534–9 (1996).
Golf, S. et al., "β–adrenoceptor density and relative number of β–adrenocentor subtypes in biopsies from human right atrial, left ventricular, and right ventricular myocard.", *Cardiovasc. Res., 19*:636–641 (1985).
Gustafson, T. et al., "Thyroid hormone regulates expression of a transfected α–myson heavy–chain fusion gene in fetal heart cells.", *Proc. Natl. Acad. Sci. U.S.A., 84*:3122–6 (1987).
Guth, B. and Dietze, T., "$I_r$ current mediates β–adrenergic enhancement of heart rate but not contractility in vivo.", *Basic Res. Cardiol., 90*:192–202 (1995).
Hajjar, R. et al., "Molecular aspects of adrenergic signal transduction in cardiac failure.",*J. Mol. Med., 76*: 747–755 (1998).
Hardouin, S. et al., "β–Adrenergic and muscarinic receptor mRNA accumulation in the sinotrial node area of adult and senescent rat heats.", *Mech. Ageing Dev., 100*: 277–297 (1998).
Holmer, S., and Homey, C., "G Proteins in the Heart: A Redundant and Diverse Transmembrane Signaling Network.", *Circulation, 84*:1891–1902 (1991).

(List continued on next page.)

Primary Examiner—Deborah Crouch
Assistant Examiner—Thaian N. Ton
(74) *Attorney, Agent, or Firm*—Hamilton, Brook, Smith & Reynolds, P.C.

(57) ABSTRACT

Molecularly-mediated and cellular-based β-adrenergic receptor-dependent biological pacemakers are disclosed. Methods of using these compositions to improve cardiac chrontropic responsiveness by upregulating heart rate and altering cardiac rhythm are also disclosed.

6 Claims, 5 Drawing Sheets

OTHER PUBLICATIONS

Inglese, Jr. et al., "Structure and Mechanism of the G Protein–coupled Receptor Kinases.", *J. Biol. Chem.*, 268:23735–23738 (1993).

Iwaki, K. et al., "α– and β–Adrenergic Stimulation Induces Distinct Patterns of Immediate Early Gene Expression in Neonatal Rat Myocardial Cells.", *J. Biol. Chem.*, 265:13809–17 (1990).

Johns, D. et al., "Adenovirus–mediated Expression of a Voltage–gated Potassium Channel In Vitro (Rat Cardiac Myocytes) and In Vivo (Rat Liver).", *J. Clin. Invest.*, 96:1152–8 (1995).

Kass–Eisler, A. et al., "Quantitative determination of adenovirus–mediated gene delivery to rat cardiac myocytes in vitro and in vivo.", *Proc. Natl. Acad. Sci. U.S.A.*, 90:11498–502 (1993).

Kitsis, R. et al., "Hormonal modulation of a gene injected into rat heart in vivo.", *Proc. Natl. Acad. Sci. U.S.A.*, 88:4138–42 (1991).

Kitsis, R and Leinwand, L., "Discordance between gene regulation in vitro and in vivo.", *Gene Expr.*, 2:313–8 (1992).

Koh, G. et al., "Targeted Expression of Transforming Growth Factor–β1 in Intracardiac Grafts Promotes Vascular Endothelial Cell DNA Synthesis.", *J. Clin. Invest.*, 95:114–121 (1995).

Koh, G. et al., "Stable Fetal Cardiomyocyte Grafts in the Hearts of Dystrophic Mice and Dogs.", *J. Clin. Invest.*, 96: 2034–2042 (1995).

Kohout, T. et al., "Novel Adenovirus Component System That Transfects Cultured Cardiac Cells with High Efficiency.", *Circ. Resp.*, 78:971–7 (1996).

Labhasetwar et al., "A DNA Controlled–Release Coating for Gene Transfer: Transfection in Skeletal and Cardiac Muscle.", *J. Pharm. Sci.*, 87: 1347–1350 (1998).

Lapointe, M. et al., "Upstream Sequences Confer Atrialspecific Expression on the Human Atrial Natriuretic Factor Gene.", *J. Biol. Chem.*, 263:9075–9078 (1988).

Lee, J. et al., "Cardiac and Pulmonary Replacement: Cardiac Gene Transfer by Instracoronary Infusion of Adenovirus Vector–Mediated Reporter Gene in the Transplanted Mouse heart.", *J Thorac. Cardiovasc. Surg.*, 111:246–52 (1996).

Lefkowitz, R. and Caron M., "Adrenergic Receptors: Models for the Study of Receptors Coupled to Guanine Nucleotide Regulatory Proteins.", *J. Biol. Chem.*, 263:4993–6 (1988).

Leor, J. et al., "Transplantation of Fetal Mycardial Tissue Into the Infarcted Myocardium of Rat.", *Circulation*, 94:11332–11336 (1996).

Lohse, M. et al., "Mechanisms of β–adrenergic receptor desensitatization: from molecular biology to heart failure.", *Basic Res. Cardiol.*, 91:29–34 (1996).

Mansier, P. et al., "Decreased heart rate variability in transgenic mice overexpressing atrial $\beta_1$–adrenoceptors.", *Am. Phys. Soc.*, 96:H1465–H72 (1996).

Milano, C. et al., "Enhanced Myocardial Function in Transgenic Mice Overexpressing the $\beta_2$–Adrenergic Receptor.", *Science*, 264:582–6 (1994).

Molenaar, P. et al., "Function, Characterization and Autoradiographic Localization and Quantification of β–Adrenoceptors in Cardiac Tissues.", *Clin. Exp. Pharamacol. Physiol.*, 16:529–533 (1989).

Moxham, C. et al., "Mammalian $\beta_1$– and $\beta_2$—Adrenergic Receptors: Immunological and Structural Comparisons.", *J. Biol. Chem.*, 261: 14562–14570 (1986).

Pennock, G. et al., "Identification of Simple Substituted Phenols with Thyromimetic Activity: Cardiac Effects on 3,5–Diiodo–4–Hydroxyphenylpropionic Acid[1].", *J. Pharmacol. Exp. Ther.*, 268:216–23 (1994).

Rossi, M., "Chronic Hemodynamic Unloading Regulates the Morphologic Development of Newborn Mouse Hearts Transplanted into the Ear of Isogeneic Adult Mice.", *Am. J. Pathol.*, 14:183–91 (1992).

Saito, K. et al., "Characterization of $\beta_1$—and $\beta_2$–adrenoceptor subtypes in the rat sinoatrial node and stellate ganglia by quantitative autoradiography.", *Neurosci. Lett.*, 96:35–41 (1989).

Savarese, T., and Fraser, C., "In vitro mutagenesis and the search for structure–function relationships among G protein–coupled receptors.", *Biochem. J.*, 283:1–19 (1992).

Selye, H. et al., "Simple Techniques for the Surgical Occlusion of Coronary Vessels in the Rat.", *Angiology*, 11:398–401 (1960).

Sen, A. et al., "Inhibition of the Release of Arachidonic Acid Prevents the Development of Sarcolemmal Membrane Defects in Cultured Rat Myocardial Cells during Adenosine Triphosphate Depletion.", *J. Clin. Invest.*, 82:1333–8 (1998).

Wolff, J. et al., "Direct Gene Transfer into Mouse Muscle In Vivo.", *Science*, 247:1465–8 (1990).

Xiao, R. et al., "Age–associated Reduction in Cardiac $\oplus_1$—and $\beta_2$–Adrenergic Responses Without Changes in Inhibitory G Proteins or Receptor Kinases.", *J. Clin. Invest.*, 101: 1273–1282 (1998).

Ye, X. et al., "Regulated Delivery of Therapeutic Proteins After in Vivo Somatic Cell Gene Transfer.", *Science*, 283:88–91 (1999).

\* cited by examiner

ENHANCEMENT OF CARDIAC CHRONOTROPY

RELATED APPLICATION

This application is a Continuation of PCT Application No. PCT/US99/00732, filed on Jan. 13, 1999, which claimed priority to U.S. Provisional Application Serial No. 60/071,456, filed Jan. 13, 1998, entitled "Enhancement of Cardiac Chronotropy", the entire teachings of which are incorporated herein by reference.

GOVERNMENT SUPPORT

This invention was made with government support under Grant Number NIH-2P01-HL41484 awarded by the National Institutes of Health. The government has certain rights in the invention.

BACKGROUND OF THE INVENTION

The natural pacemaker of the mammalian heart is the sinoatrial node (SA node) which is located in the high right atrium, and which comprises specialized pacemaker cells that generate electrical impulses characterized by an intrinsic rhythm. The electrical impulse, or pacemaker potential results from the spontaneous depolarization (a bioelectrical process involving the influx and egress of ions which reduces a membrane potential to a less negative value) of the cardiomyocytes within the SA node. This depolarization spreads from the sinus node through the surrounding atrial tissue and then into the atrial-ventricular node (AV node) before proceeding into the ventricular conduction system. Cardiac chronotropic incompetence resulting from cardiac conduction pathway dysfunction results in abnormalities of the cardiac cycle which are commonly referred to as arrhythmias.

It has been demonstrated that $\beta$-adrenergic receptors ($\beta$AR) regulate cardiac myocyte inotropic and chronotropic responses through a G protein-linked signaling pathway (Holmer, S. R., and Homcy, C. J., *Circulation*, 84(5):1891–1902 (1991); Inglese, J. et al., *J Biol Chem.* 268(32):23735–23738 (1993); Lefkowitz, R. J., and Caron, M. G., *J Biol Chem.* 263(11):4993–6 (1988)). These signaling pathways involve both $G_{\alpha s}$-direct and cAMP-mediated interactions with ion channels involved in myocyte depolarization. Stimulation of $\beta$AR increases heart rate as well as cardiac inotropic force. Conversely, blockade of $\beta$AR decreases heart rate and cardiac contractility. Cardiac chronotropic incompetence is associated with an increased prevalence of morbidity and mortality.

The majority of the causes of chronotropic incompetence require the implantation of an electronic pacemaker, either temporarily or permanently. The dangers of such surgical procedures are well known. Furthermore, electronic pacemaker devices are subject to failure, which necessitates subsequent surgical procedures to replace the defective device. Future treatments for chronotropic incompetence may be based on therapeutics (biological pacemakers) which can specifically enhance the pacemaker potential of endogenous cardiac tissue. Therefore, it is useful to provide novel compositions and alternative methods to alleviate chronotropic incompetence without the necessity of surgical intervention.

SUMMARY OF THE INVENTION

The present invention relates to compositions and methods for regulating heart rate comprising localized introduction (e.g., delivery) of one or more exogenous genes to cardiac tissue. Specifically encompassed by the present invention are methods employing gene therapy strategies to provide molecular-mediated or cellular-based biological pacemakers to treat cardiac chronotropic and conduction disorders. The resulting ability to reconstitute the function of defective $\beta$-adrenergic signaling cascade in the myocardial tissue localized to the SA node of patients with arrhythmias, cardiac disease, or age-associated myocardial dysfunction offers great hope for the reduction of morbidity and mortality.

As described herein, a murine cDNA chronotropic test system was developed to evaluate the effects of expressing the human $\beta_2$-adrenergic receptor ($\beta_2$AR) in mice under in vitro, ex vivo and finally in vivo conditions. The ability of $\beta_2$AR gene therapy to restore the normal function of endogenous cardiac tissue was further evaluated in a direct porcine cardiac gene therapy system. More specifically, the present invention describes a gene therapy strategy which utilizes localized expression of biological pacemakers to restore the function of the $\beta$-adrenergic signaling cascade. The strategy results in improved cardiac performance and is a useful modality to restore the chronotropic and inotropic responsiveness of dysfunctional or senescent mammalian cardiac tissue.

In one embodiment, the biological cardiac pacemaker is a molecularly-mediated pacemaker. The molecularly-mediated pacemaker is an expression construct comprising at least one gene encoding a cellular protein which either upregulates heart rate, alters cardiac rhythm, or encodes a receptor protein or signal transduction molecule which is essential to normal physiologic cardiac conductance. The gene, or genes, are operably linked to expression control sequences. The expression construct comprising the molecularly-mediated pacemaker can mediate either transient or stable expression. For example, the molecularly-mediated pacemakers can be transiently expressed, and can comprise at least one gene selected from the group consisting of a $\beta_2$AR gene, a$\beta_1$AR gene, and a $G_{\alpha s}$ gene. The gene can encode either the endogenous protein or a heterologous protein which is sufficiently homologous to the endogenous protein to possess biological activity in the recipient host cell. In an alternative embodiment, the molecularly-mediated pacemaker can comprise at least one gene selected from the above listed group operably linked to expression control sequences suitable for transient expression under the control of a cardiac tissue specific promoter, which can be either constitutive or inducible. In a further embodiment the cardiac tissue promoter can be specific for atrial tissue.

The invention also pertains to a cellular-based biological cardiac pacemaker utilizing genetically modified cells. A cellular-based cardiac pacemaker can comprise at least one cell transfected or transduced with at least one gene that upregulates heart rate or alters cardiac rhythm, for example a $\beta_2$AR gene a $\beta_1$AR gene or a $G_{\alpha s}$ gene.

The invention also encompasses methods of regulating in vivo cardiac pacemaking (chronotropic) activity in a mammal by introducing one of the biologic cardiac pacemakers described herein into the SA node region of an endogenous mammalian heart. The mammal for example be a human. The biological pacemaker is introduced into the heart of the mammal, for example, into the right atrium at a site which is localized to a region surrounding the sinoatrial node. The chronotropic method can employ a molecularly-mediated cardiac biological pacemaker comprising at least one gene that upregulates heart rate or alters cardiac rhythm under the control of expression control elements which mediate either transient expression or stable expression, which is either constitutive or inducible.

Cardiac pacemaking activity can also be controlled by a method employing a cellular-based cardiac biological pacemaker comprising at least one myocyte transfected or transduced with at least one gene that upregulates heart rate or alters cardiac rhythm introduced (transplanted or grafted) into the SA node region of the right atria of the recipient host mammal.

The cardiac chronotropy methods described herein can be used for an individual suffering from cardiac conductive tissue incompetence (arrhythmias) indicative of a underlying disorder of cardiac impulse generation, or to treat an older patient experiencing age-related defects in cardiac performance. For example, the method may be useful in clinical conditions characterized by an abnormal sinus rhythm including but not limited to individuals having sick sinus syndrome, sinus bradycardia, or heartblock.

The methods can also be used for permanently regulating cardiac pacemaking activity in a mammal by introducing a stable cellular-based cardiac pacemaker comprising at least one myocyte transfected or transduced with at least one gene that upregulates heart rate or alters cardiac rhythm, or by introducing an molecularly-mediated cardiac pacemaker transcriptionally regulated for stable expression under the control of an inducible promoter.

The invention also encompasses methods of enhancing the basal heart rate of a mammal by delivery into the mammal of a biological pacemaker comprising exogenous genes which upregulate heart rate or alters cardiac chronotropic or inotropic responsiveness. The invention further encompasses methods of enhancing (upregulating) inotropic responsiveness (cardiac function) of cardiac tissue by utilizing one of the biological cardiac pacemakers described herein to upregulate heart rate or cardiac rhythm.

The chronotropic regulatory methods may further employ the in vivo administration of a receptor agonist having a specific cellular affinity for the molecule mediating the chronotropic or inotropic effect. For example, if the activity of the biological pacemaker is based on the expression of $\beta_2$AR, the method could further comprise the systemic or local administration of a cardioselective β-adrenergic agent such as isoproterenol.

Future treatments for chronotropic incompetence may obviate the need for mechanical pacemakers, by employing gene therapy strategies to develop therapeutics (biological pacemakers) which can specifically enhance the pacemaker potential of endogenous cardiac tissue. Therefore, it is useful to provide novel compositions and alternative methods are available to alleviate chronotropic incompetence without the necessity of surgical intervention, and the associated risk of mechanical or electronic failure.

DETAILED DESCRIPTION OF THE INVENTION

Figure 1A:
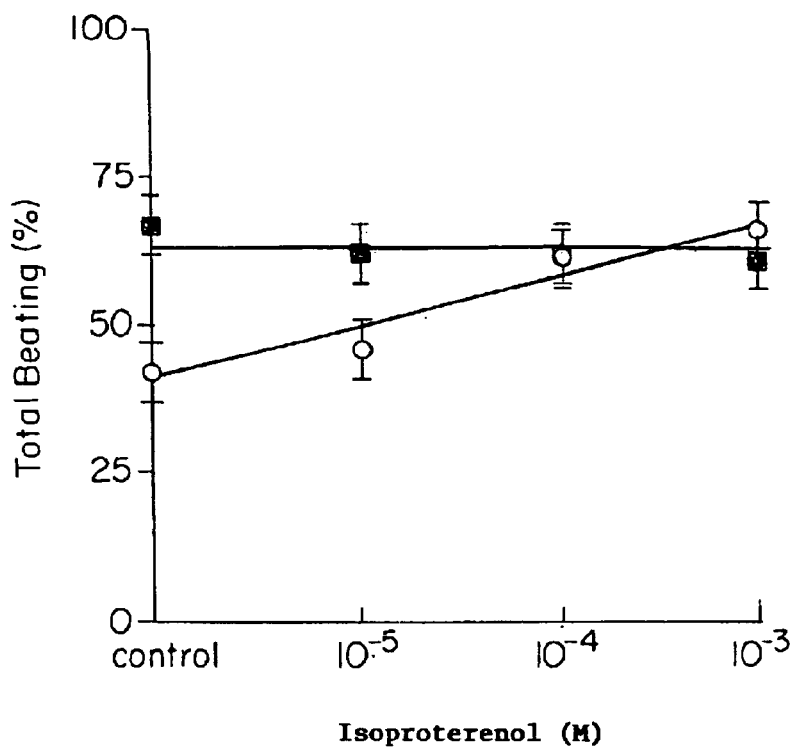
FIGS. 1A and 1B are graphs depicting the results of an experiment showing in vitro cardiac myocyte chronotropic recruitment. A. The percentage of cardiac myocytes contracting, in the $\beta_2$AR transfected cells (black boxes) and control cells (white circles), in the presence of increasing concentrations of isoproterenol ($0-10^{-3}$ M). B. The percentage of cardiac myocytes with a chronotropic rate greater than 60 bpm, in the $\beta_2$AR transfected (black boxes) and control cells (white circles), in the presence of increasing concentrations of isoproterenol ($0-10^{-3}$ M).

The physiologic depolarization of the heart originates in the sinus node located in the high right atrium. This depolarization spreads from the sinus node through the surrounding atrial tissue and then into the atrial-ventricular node before proceeding into the ventricular conduction system. The rate of sinus node depolarization results from the spontaneous depolarization of myocytes within the node (DiFrancesco, D., *Nature*, 324(6096):470–473 (1986)). These spontaneous cellular depolarizations are automatic, and are, in turn, subject to both sympathetic and parasympathetic regulation. Myocytes from other areas of the heart also depolarize spontaneously, but at physiologic frequencies significantly lower than those of sinus nodal myocytes. Thus, impulses originating from sinus node depolarization suppress the spontaneous activity of myocytes in other areas. Increased activation of the sinus node elevates heart rate, whereas depressed activation of sinus node may lead to cardiac activation by impulses originating from other areas of the heart.

β-adrenergic receptors belong to a large family of G-protein coupled receptors characterized by a homologous structure which includes seven transmembrane domains. Three isoforms of β-adrenergic receptors, designated $\beta_1$-$\beta_2$- and $\beta_3$-adrenoreceptors have been cloned from mammalian tissue (Hajjar, R. J. et al., *J. mol. Med.* 76: 747–755 (1998)). The cardiac β-adrenoreceptor signaling pathway is made up of the $\beta_1$- and $\beta_2$-adrenoreceptor, which are coexpressed in the myocardium. Extensive previous research has demonstrated that β-adrenergic receptors (βAR) regulate cardiac myocyte inotropic and chronotropic responses through a G protein-linked signaling pathway (Holmer, S. R., and Homcy, C. J., *Circulation*, 84(5):1891–1902 (1991); Inglese, J. et al., *J Biol Chem.* 268(32):23735–23738 (1993); Lefkowitz, R. J., and Caron, M. G., *J Biol Chem.* 263(11):4993–6 (1988)). The β-adrenergic receptor (βAR) system plays a major role in cardiac contraction. These signaling pathways involve both $G_{\alpha s}$-direct and cAMP-mediated interactions with ion channels involved in myocyte depolarization. Agonist-mediated stimulation of the βAR activates adenylyl cyclase and triggers the production of cyclic adenosine-3'5' monophosphate. Stimulation of βAR increases heart rate as well as cardiac inotropic force. Conversely, blockade of βAR decreases heart rate and cardiac contractility. The βAR-regulated response is also seen in cultured cardiac myocytes which exhibit an increased spontaneous depolarization rate as well as an augmented contractile force.

The period of automatic depolarization of the heart is shortened by stimulation of βAR in part through an increase in the flux of diastolic depolarization current ($I_f$) in cardiac myocytes (Guth, B. D., and Dietze, T., *Basic Res Cardiol.* 90(3):192–202 (1995)). Moreover, the sinus node has a higher density of βAR compared with the surrounding atrium (Beau, S. L. et al., *Circ Res.* 77(5):957–963 (1995); Saito, K. et al., *Neurosci Lett.* 96(1):35–41 (1989)), which in turn has a higher βAR density than the rest of the heart (Golf, S. et al., *Cardiovasc Res.* 19(10):636–641 (1985). The atrioventricular conduction system also has a higher density of $β_2$-adrenoreceptors compared with the rest of the myocardium (Molenarr, P. et al., *Clin. Exp. Pharmacol. Physiol.* 16(6): 529–533 (1989). The expression pattern of βARs, and the regulation of their $I_f$ current, suggest that increasing the density of βARs expressed in the vicinity of the sinus node will mediate an increase in heart rate.

Heart failure is often characterized by a markedly reduced responsiveness of the β-adrenergic receptor-dependent signaling system and a decreased positive inotropic responsiveness (Lohse, M. J. et al., *Basic Res. Cardiol.* 91(*Suppl.* 2): 29–34 (1996)). Abnormalities in the β-adrenergic signaling cascade have been associated with impaired inotropic responsiveness in patients with congestive heart failure (CHF) (Drazner, M. H. et al., *Proc. Assoc. Am. Physicians* 109(3) 220–227 (1997)), and patients with cardiac valve disease (CVD) frequently have CHF associated with chronic myocardial βAR desensitization due to persistent exposure to increased circulatory catecholamine levels (Gerhardt, M. A. et al., *Circulation* 98(Suppl): II 275–281 (1998)). In addition, quantitative changes in the expression of genes encoding βAR subtypes in the sinoatrial area of the senescent (aging) heart has been postulated as a determinant of age-associated modifications in heart rate variability and diminished contractile response(Xiao, R. P. et al, *J. Clin. Invest.* 101(6): 1273–1282 (1998); Hardouin, S. et al, *Mech. Ageing Dev.* 100 (3): 277–297 (1998)). Recent studies investigating the role of the β-adrenergic signaling cascade in the aging heart report a nonselective downregulation of both β1- and β2-adrenoreceptor isoforms leading to a proportional decrease in receptor density with age which is in turn accompanied by a decreased sensitivity to noradrenaline (Xiao, R. P. et al., *J. Clin. Invest.* 101: 1273–1282 (1998)). This data suggest that in the aging heart, decreased βAR density may be of primary import in the decline of positive inotropic responsiveness. In the human heart, the β-adrenergic receptor-G-protein adenylyl cyclase system is possibly the most powerful physiological mechanism available to acutely increase either heart rate and/or contractility (Brodde, O. E., *Basic Res. Cardiol.* 91 *Suppl.* 2:35–40 (1996)).

The βARs are excellent targets for directed localized gene expression in the mammalian heart. The human $β_2$AR is a particularly attractive target for expression in murine model systems, as it is immunologically distinct from, yet structurally and functionally similar to the murine receptor (Moxham, C. P. et al., *J Biol Chem.* 261(31):14562–14570 (1986); Chung, F. Z. et al., *FEBS Lett.* 211(2):200–206 (1987); Savarese, T. M., and Fraser, C. M., *Biochem J.* 283 (Pt 1):1–19 (1992)). Transgenic mice constructed with the α-MHC promoter fused to human $β_2$AR result in mice overexpressing $β_2$AR throughout the heart (Milano, C. A. et al., *Science*, 264(5158):582–6 (1994)). These transgenic mice manifest enhanced myocardial function with increased heart rate and cardiac inotropy. A transgenic based chronotropism model is limited by the practical limitation that a $β_2$AR-mediated increase in cardiac chronotropy cannot be separated from an inotropic effect. Therefore, it is difficult to utilize a transgenic model to determine whether a local gene expression strategy designed to increase site-specific βAR density expression in the sinoatrial nodal tissue can selectively increase cardiac rate in the intact heart. The transgenic approach as an intermediate step in the evaluation of candidate genes is also significantly limited by the time period necessary for in vivo generation of the mice.

The Examples presented herein demonstrate that local elevation of $β_2$AR density in the right atrium by direct gene transfer increases the rate of the heart (a chronotropic effect). A model evaluation system comprising assays of increasing complexity to assess other candidate genes under in vitro, ex vivo, and finally in vivo conditions was established. This integrated approach permits the prolongation/ optimization of the effect of transferred exogenous genes on basal heart rate and cardiac rhythm, which will be helpful in most contemplated practical usages.

The Examples provided herein provide a combination of in vitro, ex vivo, and in vivo gene transfer techniques useful for the to identification and characterization of genes that could be employed to selectively upregulate heart rate and alter cardiac rhythm in an intact heart. The data presented herein demonstrate that the local delivery of expression constructs and/or molecularly engineered cells can increase cardiac pacemaking activity for varying periods of time.

Previous investigations have developed a variety of approaches for expressing exogenous genes in cardiac myocytes under in vitro and in vivo conditions. Transient transfection of isolated cells by the calcium phosphate or lipofection technique with the subsequent determination of the rate of contraction allows initial screening of candidate genes which might upregulate cardiac rate. Cardiac myocytes were derived from fetal hearts in order to take advantage of their enhanced viability and transfection frequency relative to adult-derived cells (Gustafson, T. A. et al., *Proc Natl Acad Sci USA*, 84(10):3122–6 (1987)). However, the efficiency of transfection is relatively low (3%–5%) which requires cotransfection with markers that permit selective monitoring of transfected cells. In Example 1, green flourescent protein(GFP was utilized in conjunction with inverted microscopy and epifluorescence filters to manually count the contraction rates of different classes of myocytes (spontaneously beating or fast beating cells) or a video edge motion detector to obtain the average rate of contraction of all transfected cells. Prior studies have also utilized an adenoviral system to achieve virtually complete transfection of isolated myocytes which obviates the need for marking transfected cells (Kohout, T. A. et al., *Circ Res.*, 78(6):971–7 (1996)). This latter approach has been used to overexpress the human $β_2$AR in rabbit cardiac myocytes with a documented enhancement in the relevant signaling pathway (Drazner, M. H. et al., *J Clin Invest.*, 99(2):288–96 (1997)). In similar fashion, Johns and coworkers transfected cultured rat cardiac myocytes have been transfected with an adenoviral-like vector to express a voltage-gated potassium channel (Johns, D. C. et al., *J Clin Invest.*, 96(2):1152–8 (1995)). This technique represents a powerful approach for in vitro assessment of candidate genes that upregulate heart rate or alter cardiac rhythm.

Atrial targeting of a transgene may be achieved with previously described atrial specific promoters (Field, L. J., *Science*, 239(4843):1029–33 (1988)), and has been employed to overexpress the human beta-1 adrenergic receptor (Bertin, B. et al., *Cardiovasc Res.*, 27(9):1606–12 (1993)). For example, the atrial specific atrial natriuretic factor promoter was used in the first reported murine transgenic overexpression model of human $\beta_1AR$ (Bertin, B. et al., *Cardiovasc Res.*, 27(9):1606–12 (1993)). Interestingly, the initial data from these mice, unlike the data from the $\beta_2AR$ transgenic mice, indicated no enhanced chronotropy. This effect was potentially due to pronounced down-regulation of the constitutively overexpressed receptor. Atria derived from these mice were subsequently found to possess enhanced basal function and reduced heart rate variability (Mansier, P. et al., *Am. J. Physio.* 270: 1465–1472 (1996).

Employing inducible elements in concert with the atrial specific promoter may decrease such down-regulation, and may be valuable in the final evaluation of candidate genes, particularly if their expressions could specifically be targeted to the sinus node or other critical conduction tissue. Ye et al., have recently reported the regulated (rapamycin-inducible) delivery of a therapeutic recombinant protein after in vivo somatic cell gene transfer (Ye, X. et al., *Science* 283: 88–91 (1999)). Delivery strategies such as these facilitate the stable transduction of cells and allow for the selective induction of the transgene by pharmacologic means.

As used herein the term "pacemaker" connotes an object or substance that influences the rate at which a particular phenomenon occurs. Here the relevant phenomenon is the depolarization of the sinoatrial node. As used herein the term "heart rate" refers to the number of heart beats per minute, and "heart rhythm" or "rhythm" refers to the regularity of the heart beat. The term "chronotropy" refers to the speed of impulse (electrical signal resulting from sinoatrial node depolarization) formation. The term "inotropy" refers to the force of cardiac contraction. The term "chronotropism" describes the act or process of affecting the regularity of the heart beat (or heart rate).

In one embodiment, the biological cardiac pacemaker is a molecularly-mediated pacemaker. The molecularly-mediated pacemaker is an expression construct comprising at least one gene encoding a cellular protein which either upregulates heart rate, alters cardiac rhythm, or encodes a receptor protein or signal transduction molecule which is essential to normal physiologic cardiac conductance, operably linked to expression control sequences. The expression control sequences are capable of directing expression in mammalian cells, for example in human cells. The expression construct comprising the molecularly-mediated pacemaker can be mediate either transient or stable expression. The promoters useful in constructing expression vectors useful as molecularly-mediated cardiac pacemakers may be direct either constitutive or inducible expression. A constitutive promoter directs expression under all conditions of cell growth. An inducible promoter directs expression only in the presence of an inducing agent. For example, a molecularly-mediated pacemaker can be transiently expressed, and can comprise at least one gene selected from the group consisting of a $\beta_2AR$ gene, a $\beta_1AR$ gene or a $G_{\alpha s}$ gene. The gene can encode either an endogenous protein or a heterologous protein that is sufficiently homologous to possess biological activity in the recipient host cell. In an alternative embodiment the molecularly-mediated pacemaker can comprise at least one gene selected from the above-identified group operably linked to expression control sequences suitable for transient expression under the control of a cardiac tissue specific promoter, which can be either constitutive or inducible. In a further embodiment the cardiac tissue promoter can be specific for atrial tissue.

The use of replication-deficient adenoviral viral vectors allows for a rapid assessment of candidate genes under in vivo conditions. This approach has been used with high efficiency for transduction of exogenous genes into intact or transplanted hearts (Kass-Eisler, A. et al., *Proc Natl Acad Sci USA*, 90(24):1 1498–502 (1993); Lee, J. et al., *J Thorac Cardiovasc Surg.*, 111:246–52 (1996). However, similar to the transgenic approach, the cardiac expression of adenoviral-mediated genes is widespread and cannot be employed to evaluate local effects of targeted constructs or engineered cells. The in vivo delivery of expression vectors by direct injection or lipofection has recently been extended to intact or transplanted hearts which allows local delivery of exogenous genes to the intact organ. The direct introduction of DNA with these methods has successfully modified the function of the heart in vivo, although the latter data have not always completely agreed with in vitro results (Kitsis, R. N. et al., *Proc Natl Acad Sci USA*, 88(10):4138–42 (1991); Gal, D. et al., *Lab Invest.*, 68(1):18–25 (1993); Kitsis, R. N. and L. A. Leinwand, *Gene Expr.*, 2(4):313–8 (1992)). Similarly, intravascular transfection of DNA as outlined above has also been employed to achieve local coronary arterial expression in native as well as transplanted hearts (Giordano, F. J. et al., *Nat Med.*, 2(5):534–9 (1996)). The discrepancies observed between in vivo data and in vitro results may be due to low level expression of exogenous genes in restricted areas of the heart.

The invention also pertains to a cellular-based biological cardiac pacemaker utilizing genetically modified cells. A cellular-based cardiac pacemaker can comprise at least one cell transfected or transduced with at least one gene that upregulates heart rate or alters cardiac rhythm, for example a $\beta_2AR$ gene a $\beta_1AR$ gene or a $G_{\alpha s}$ gene. Transfection refers to the acquisition by a cell of new genetic material (nucleic acid molecules) originating from an exogenous source. Transfection is usually mediated by physical or chemical means and useful protocols include, but are not limited to DEAEC-dextran mediated transfection, DNA coprecipitation, electroporation, naked plasmid adsorption and liposome-mediated transfection. Transduction refers to the process of transferring nucleic acids into a cell using a DNA or RNA viral vector. Suitable viral vectors include, but are not limited to retroviral vectors and replication-deficient adendovirus vectors. Transfection or transduction of the cells with an expression construct as described above for the molecularly-mediated embodiments of the invention can be accomplished by a variety of techniques which are well known to one of skill in the art. The invention further encompasses methods of regulating in vivo cardiac pacemaking (chronotropic) activity in an animal by introducing one of the biologic cardiac pacemakers described herein into the SA node region of an endogenous mammalian heart. The mammal, can be for example a human. The biological pacemaker is introduced into the heart, for example, into the right atrium localized to a region surrounding the sinoatrial node. The biological pacemaker composition is preferably delivered in a pharmaceutical composition comprising, for example, the molecularly-mediated expression vector in a volume of phosphate buffered saline with 5% sucrose. A therapeutically effective amount of the biological pacemaker is delivered to a site-specific location (e.g. an area in the upper portion of the right atria). A therapeutically effect amount is that amount which corrects or improves the chronotropic or inotropic defect which characterizes the recipient tissue. The therapeutically effective amount can be delivered preferably in a single administration, although multiple dose are also contemplated.

The chronotropic method can employ a molecularly-mediated cardiac biological pacemaker comprising at least one gene that upregulates heart rate or alters cardiac rhythm under the control of expression control elements which mediate transient expression. The biological pacemaker (e.g., cDNA, an expression vector or genetically-manipulated cells) can be directly injected into the myocardium in the generalized region of the sinoatrial node via a transthoracic or mini-thoracotomy procedure, or may be delivered by using a electrophysiology recording catheter modified for endocardial transfection of the cardiomyocytes located in the vicinity of the sinoatrial node.

In vivo transfection (gene transfer) into cardiac tissue can be achieved by direct intracardiac injection of plasmid DNA, or may occur pursuant to a virus-mediated gene transfer protocol (e.g. transduction) using for example modified adenoviral vectors, or hemagglutinating virus of Japan (HJV)/liposome-mediated gene transfer. HJV-liposome-mediated transfer, like adenovirus-mediated protocols do not require cell replication and thus can be used to genetically modify terminally differentiated cells such as cardiomyocytes (Ellison, K. E. et al., *J. Mol. Cell. Cardiol.* 28:1385–1399 (1996)).

Alternatively, site-specific gene delivery may be achieved using a controlled-release delivery method such as that reported by Labhasetwar et al., who describe the development of a proprietary DNA polymer solution which can be used to coat medical devices such as sutures, stents or catheters (Labhasetwar et al., *J. Pharm. Sci.* 87(11): 1347–1350 (1998)).

Site-specific delivery of a biological pacemaker described herein can also be accomplished using an electrophysiologically guided technique to identify the particular portion of the right atria where the sinoatrial node resides. One skilled in the art will be readily familiar with established cardiac mapping techniques thereby enabling them to deliver a biological cardiac pacemaker to the sinoatrial region of the right atrial chamber.

The invention also pertains to a cellular-based biological cardiac pacemaker utilizing genetically modified cells (transplanted or grafted) into the SA node region of the right atria of the recipient host mammal. A cellular-based cardiac pacemaker can comprise at least one cell transfected or transduced with at least one gene that upregulates heart rate or alters cardiac rhythm, for example a $\beta_2AR$ gene a $\beta_1AR$ gene or a $G_{\alpha s}$ gene. Transfection or transduction of the cells with an expression construct as described above for the molecularly-mediated embodiments of the invention can be accomplished by a variety of techniques which are well known to one of skill in the art. Such methods include but are not limited to transfection, adenoviral-mediated or herpes virus vector-mediated gene transfer and fusigenic liposome-mediated DNA transfer. The cells can be cardiomyocytes isolated from fetal or embryonic tissue. Alternatively the cells could be isogenic cells (e.g. cardiomyocytes, myloblasts, skeletal myocotes), cells of allogeneic cardiac-derived cell line, genetically modified skeletal myoblasts, or allogeneic or xenogenic cells which may or may not have been genetically modified to be histocompatible with the recipient host animal.

The cardiac chronotropy compositions and methods described herein can be used for an individual suffering from cardiac conductive tissue incompetence (arrhythmias) indicative of a underlying disorder of cardiac impulse generation, or to treat an older patient experiencing age-related defects in cardiac performance. For example, the method may be useful in clinical conditions characterized by an abnormal sinus rhythm including but not limited to individuals having sick sinus syndrome, sinus bradycardia, or heartblock. The method may also be useful in treating cardiac conductive disturbances responsible for atrial fibrillation, to the extent that the technique can establish a dominant alternative foci of automatic activity capable of reproducing the normal function of the sinoatrial node. Atrial fibrillation results from disorganized electrical activity in the atria. The disclosed chronotropic methods may also find utility in an individual experiencing a heart attack or transient depression of heart rate.

The chronotropic compositions and methods of the present invention can also be used for permanently regulating cardiac pacemaking activity in an animal by introducing a stable cellular-based cardiac pacemaker comprising at least one myocyte transfected or transduced with at least one gene that upregulates heart rate or alters cardiac rhythm, or by introducing a molecularly-mediated cardiac pacemaker which is transcriptionally regulated under the control of an inducible promoter. The feasibility of this approach is consistent with the observation that the targeted expression of transforming growth factor $\beta$-1 by the delivery of intracardiac grafts comprising genetically modified skeletal myoblasts, has been shown to effect the local, long-term delivery of a recombinant molecule to the heart (Koh, G. Y. et al., *J. Clin. Invest.* 95(1):114–121 (1995)). Viable syngeneic grafts were observed as long as three months after implantation, and immunohistochemical analysis confirmed the presence of grafted cells stably expressing TGF-$\beta$1. Furthermore, the ability to establish a stable intracardiac graft in a large species has been demonstrated by studies documenting the successful formation of stable fetal cardiomyocyte grafts in the myocardium of dystophic dogs (Koh, G. Y. et al., *J. Clin. Invest.* 96(4):2034–2042 (1995)). Engrafted fetal cardiomyocytes, which were identified by dystrophin immunoreactivity, were observed to be tightly juxtaposed with host cardiomyocytes as long as 10 weeks after engraftment.

The invention also encompasses methods of enhancing the basal heart rate of a mammal by delivery into the mammal of a biological pacemaker comprising exogenous genes which upregulate heart rate or alters cardiac chronotropic or inotropic responsiveness. The invention further encompasses methods of enhancing (upregulating) inotropic responsiveness of cardiac tissue by utilizing one of the biological cardiac pacemakers described herein to upregulate heart rate or cardiac rhythm.

The chronotropic regulatory methods may further employ the in vivo administration of a receptor agonist having a specific cellular affinity for the molecule mediating the chronotropic or inotropic effect. As used herein the term "agonist" means a drug that has an affinity for, and whose binding to, a cell surface receptor, triggers a biochemical response which mediates a physiologic activity. For example, if the activity of the biological pacemaker is based on the expression of $\beta$2AR, the method can further comprise the systemic or local administration of a cardioselective agent, such as a $\beta$-adrenergic agonist, for example isoproterenol.

As described in Example 1, transient transfection of cultured myocytes with expression vectors and lipofectamine was employed as the initial screen for assessing candidate genes that upregulate heart rate or alter cardiac rhythm. In Example 2, a similar approach was utilized to locally deliver exogenous genes to the intact contracting murine heart transplanted into the mouse ear which permits a rapid appraisal of the action of the candidate gene at the whole organ level that can be used for rapid evaluation of multiple constructs. In Example 3, the exogenous gene was injected into the right atrium of the intact murine heart to determine its effect on heart rate and cardiac rhythm under conditions approaching the situation under which it will be ultimately utilized. In Example 4, a porcine cardiac gene transfer system was established to evaluate the use of biological pacemakers in the endogenous heart of a large animal. The Yorkshire pig was specifically chosen for these experiments for its anatomic and physiologic similarity to the human cardiovascular system. Moreover, the porcine model has been successfully been employed in gene therapy studies involving cardiac vasculature. This system also provided an opportunity to develop a transvenous catheter delivery approach that could potentially be employed in human clinical trials.

The expression of the human $\beta_2$AR in isolated murine fetal myocytes led to a significant recruitment of cardiac cells to both spontaneously contract as well as to beat at a higher rate. This suggests that the expression of $\beta_2$AR leads to both increased automatic depolarization of myocytes as well as a higher steady state signaling through the receptor. The latter result is in accord with recent studies in which adenoviral-mediated overexpression of human $\beta_2$AR in rabbit cardiac myocytes generates raised adenylate cyclase activity (Drazner, M. H. et al., *J Clin Invest.*, 99(2):288–96 (1997)). The addition of the adrenergic agonist isoproterenol recruited a higher percentage of control myocytes to the contractile state, but did not alter the percentage of contracting $\beta_2$AR transfected cells. Moreover, saturating levels of isoproterenol, $10^{-3}$ M, raise the same percentage of myocytes to the higher contractile rate in both $\beta_2$AR transfected and control myocytes. The concentration of isoproterenol required to achieve maximal stimulation is similar to levels of agonist used in previous studies employing embryonic cardiac myocytes (Barnett, J. V. et al., *J Biol Chem.*, 264 (18):10779–86 (1989); Pennock, G. D. et al., *J Pharmacol Exp Ther.*, 268(l):216–23 (1994)). Finally, the above level of agonist increased the average contractile rate of the $\beta_2$AR tansfected myocytes to significantly higher levels as compared to control cells. These data suggest that enhanced signaling through $\beta_2$AR overexpression leads to an increased rate of spontaneous cardiac myocyte beating, as well as an increased extent of steady state signaling which further augments the rate of contraction. These two effects are induced in control cells by addition of isoproterenol, and the employment of the agonist in combination with transfection allows an augmented response to the drug.

The in vitro experiments outlined above served as an excellent foundation for extending the investigation to the next phase of the evaluation. The results obtained with cultured cardiac myocytes transfected with the $\beta_2$AR suggested that expression of the receptor in cardiac tissue should result in an increased heart rate. The above hypothesis was initially tested in an ex vivo model, described in Example 2. The transplanted neonatal hearts served as an intermediate test in the progression from in vitro to in vivo models of $\beta_2$AR gene tansfer. The subdermally transplanted heart, as compared to the native heart, possesses the advantage of being easily accessible which permits injection of constructs under direct observation without the need for complex surgical procedures. Furthermore, ECGs of the transplanted hearts can be recorded from leads attached to the host ear, and are electrically isolated from the host heart which can be utilized as a control.

The injection of transplanted hearts with constructs encoding the $\beta_2$AR elevated the basal rate of cardiac contraction of the transplanted heart for several days, presumably during the expression of the $\beta_2$AR construct with no other additional alterations in the ECG. These results demonstrate that the in vitro observations of $\beta_2$AR-mediated enhancement of myocyte chronotropy are predicative of the ability of the transferred exogenous gene to increase basal heart rate in the whole organ. The effects of $\beta_2$AR on the spontaneous depolarization of myocytes are of particular importance in this regard. Moreover, the above results suggest that injection of candidate genes into transplanted hearts serve as an excellent model for testing cardiac gene therapy targets.

In Example 3, $\beta_2$AR constructs were injected into the right atrium of native murine hearts and were observed to generate a marked increase in cardiac rate as compared to control plasmids for several days presumably during the expression of the $\beta_2$AR construct. Similar to observations made with the ex vivo model, minimal changes were noted in the electrocardiograms of $\beta_2$AR transfected hearts except for the increased basal rate. The expression of the encoded human $\beta_2$AR is confined to the right atrium of the injected hearts, as demonstrated by immunohistochemical analyses which suggests that $\beta_2$AR-enhanced stimulation is initiated in the right atrium and then proceeds through the normal conduction system of the heart.

In Example 4, constructs encoding either the human $b_2$ adrenergic receptor ($\beta_2$AR) or green fluorescent protein (GFP) were injected into the right atrium of native Yorkshire pig hearts. The $\beta_2$AR construct significantly enhanced chronotropy, as compared to control injections. The average cycle length of the pig heart rate was 567+/−100 ms prior to injection. Two days after injection with plasmid encoding the $\beta_2$AR the cycle length decreased to 327+/−60 ms, as compared to the control cycle length 488+/−130 ms (p<0.03). The difference in cycle length after control injection was not statistically significant (p>0.3). These changes correlated with a 49% increase in the average heart rate in the $\beta_2$AR injected pigs (183+/−28 vs. 122+/−25 bpm). The increased heart rate was sustained for 1 to 2 days after which the heart rate trended to baseline levels. Sections of the right atrial tissue at the site of injection revealed the presence of GFP. Immunostaining of the sections revealed a colocalization of the human $\beta_2$AR in the co-injected with the $\beta_2$AR-encoding constructs confirming that the injection of the cDNA constructs resulted in the expression of the encoded genes. These studies further demonstrate that local targeting of gene expression is a feasible modality to regulate the cardiac pacemaking activity.

In summary, these investigations provide an integrated experimental approach for identifying candidate genes and developing local delivery approaches for maximizing and/or prolonging the effects of these candidate genes in upregulating heart rate and altering cardiac rhythm. The results suggest that the above approaches are useful in the development of both molecularly-mediated and cellular-based cardiac pacemakers.

The following examples are offered for the purpose of illustrating the present invention and are not to be construed to limit the scope of the invention. The teachings of all references cited herein are hereby incorporated by reference.

EXAMPLES

Example 1

Transfection of Murine Myocytes Plasmid Constructs:

The human $\beta_2$AR cDNA was a gift from Dr. Robert J. Leftowitz (Duke University Medical Center). A 2.25 kb Sal1-BamH1 fragment of the human $\beta_2$AR cDNA was ligated into a Sal1-BamH1 site 3' to the $\beta$ actin promoter ($\beta$AP) in a pBR322 vector to generate pBR322-$\beta$AP-$\beta_2$AR-SV40. In similar fashion, the bacterial $\beta$-galactosidase gene (LacZ) was ligated to the $\beta$AP in a pBR322 vector and served as a control expression vector. The plasmid phGFP-S65T encoding the green fluorescent protein (GFP) was purchased from Clontech (Palo Alto, Calif.).

Myocyte Harvest

Cultured fetal murine myocardial cells were prepared as previously described (Iwaki, K. et al., *J Biol Chem.*, 265 (23):13809-17 (1990); Sen, A. et al., *J Clin Invest.*, 82 (4):1333-8 (1988)). Myocytes from ventricles of 17.5 day old B6D2F1 fetal mice were fragmented with a straight-edge razor. The tissue was then digested with 0.5 mg/ml collagenase II (Worthington Biochemical Corp., Freehold, N.J.) and 1.0 mg/ml pancreatin (Sigma Chemical Co., St. Louis, Mo.) in ADS buffer (116 mM NaCl, 20 mM HEPES, 1 MM NaH$_2$PO$_4$, 5.5 mM glucose, 5.4 mM KCl, 0.8 mM MgSO$_4$, pH 7.4) at 37° C. for 10 min. The cells were centrifuged at 700 g at 4° C. for 5 min. The cells were then plated onto 48-well plates (Falcon Labware, Cockeysville, Md.) pre-coated with 1% gelatin or onto 25 mm$^2$ square coverslips precoated with 1% gelatin and 20 $\mu$g/ml laminin at a density of $10^5$ cell/ml in Dulbecco's modified Eagle's media (DMEM) supplemented with 10% fetal calf serum (FCS), and Streptomycin 100 $\mu$g/ml, and Penicillin (500 $\mu$g/mL). The myocytes were grown at 37° C. in 5% CO$_2$.

In Vitro Myocyte Transfection

The transfection of myocytes with lipofection was optimized. Myocytes were plated as described above and grown overnight. The $\beta_2$AR, LacZ, or GFP expression circular vectors (1:2.5 M/M; 0.125 $\mu$g total DNA/well) were incubated with Lipofectamine (Life Technologies) (12.5 $\mu$l/well) in Opti-Mem I (Life Technologies) reduced serum medium (12.5 $\mu$l/well) for 30 min at 25° C. After incubation, DMEM (100 $\mu$l/well) was added. The myocyte cultures were washed with PBS twice, the Lipofectamine-DNA mixtures were added, and the cultures incubated at 37° C. After 4 hours, an equal volume of DMEM with 20% FCS was added to the cultures. The cultures were incubated overnight and the medium was changed to DMEM with 10% FCS.

The myocytes were assayed 48 hr after transfection. Myocytes cotransfected with GFP were identified by inverted microscopy employing epifluorescence filters for FITC$_{(excitation\ 405\ nm/emission\ 490\ nm)}$. Expression of either human $\beta_2$AR or LacZ was confirmed by immunostaining or X-gal staining, respectively. Immunostaining for the human $\beta_2$AR was performed with a rabbit-antihuman $\beta_2$AR polyclonal antibody (Santa Cruz Research, Santa Cruz, Calif.), which does not cross-react with the murine receptor. The myocyte cultures were washed with PBS and blocked with 10% normal serum in PBS for 20 min. Samples were then incubated with the primary antibody at 1.0 $\mu$g/mL in PBS with 1% bovine serum albumin for one hr in a humid chamber at 25° C. The sample was then washed with PBS three times and then incubated with the secondary donkey anti-rabbit Cy3 polyclonal antibody (Jackson ImmunoResearch, West Grove, Pa.) at a 1:1000 dilution in PBS with 1% bovine serum albumin for one hr in a humid chamber at room temperature. The samples were washed with PBS three times and mounted with 90% glycerol in PBS.

Myocyte Contraction Rate Determination

The percentage of beating myocytes was determined for cells transfected with either the $\beta_2$AR expression vector or the control construct. The myocytes were identified by GFP as described above. The total percentage of beating cells ($\geq 1$ contraction/minute) was estimated visually from cotransfected GFP-positive myocytes (>100 cells/point). In addition, the percentage of myocytes that were beating faster than 60 beats per minute (bpm) was determined in identical fashion. Similar measurements of the percentages of both total and fast beating myocytes were conducted at various concentrations of isoproterenol (control, $10^{-5}$, $10^{-4}$, and $10^{-3}$ M). Both the total percentage of beating myocytes and those with rates>60 bpm were used as a measure of automaticity.

The average rate of myocyte contraction was quantitated by motion detector under both baseline and $10^{-3}$ M isoproterenol. Inverted microscopy with epifluorescence filters for FITC$_{(excitation\ 405\ nm/emission\ 490\ nm)}$ and a video edge motion detector (Cresecent Electronics) were employed to determine the average rate of the contractions of GFP-positive myocytes. The statistical significance of the increased rate of myocyte contraction was determined by Student's t-Test analysis.

Results

Myocyte Contractile Recruitment

The percentage of cardiac myocytes that beat under baseline conditions was higher in the population of cells transfected (3–5% efficiency) with the $\beta_2$AR expression vector, as compared with the control LacZ expression vector. FIG. 1A shows that under baseline conditions 67% of the $\beta_2$AR transfected myocytes exhibit spontaneous contractions as compared with 42% in the control LacZ transfected cells. The addition of increasing concentrations of isoproterenol elevated the percentage of control LacZ transfected myocytes to 69%, which is similar to the percentage of $\beta_2$AR transfected cells contracting at baseline. Moreover, the addition of isoproterenol failed to increase the number of contracting $\beta_2$AR transfected myocytes.

Figure 1B:
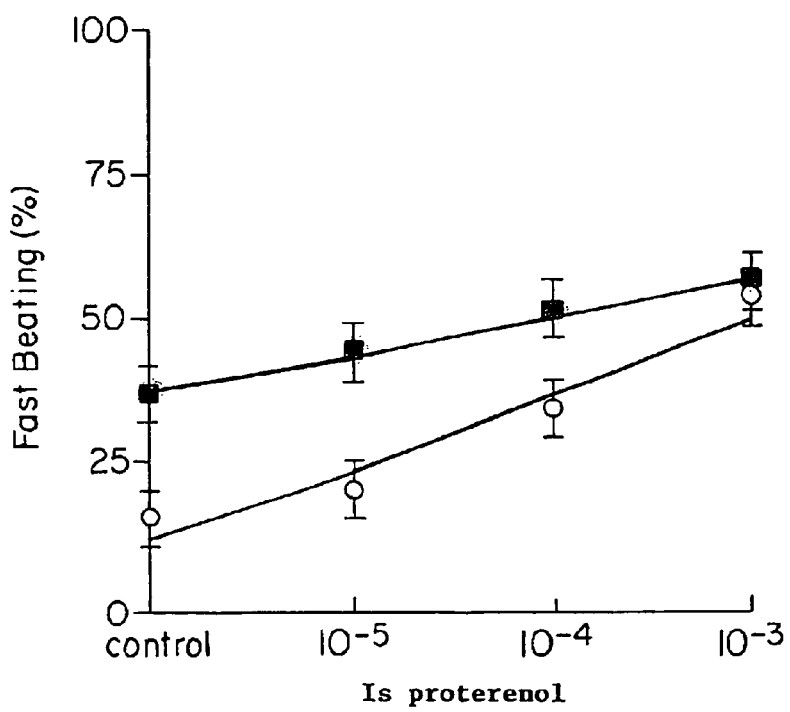

The percentage of myocytes with chronotropic rates greater than 60 bpm (fast beating cells) was higher in the $\beta_2$AR transfected myocytes as compared with the control transfected cells. FIG. 1B shows that in the absence of isoproterenol 37% of the $\beta_2$AR transfected cells beat fast as compared with 15% of the control transfected cells. As compared to the total percentage of contracting cells, the number of fast beating cells increased in both the $\beta_2$AR and control populations with addition of isoproterenol. At $10^{-3}$ M isoproterenol, the percentage of $\beta_2$AR transfected cells increased to 57%, which was not different from the response of the control transfected cells (54%).

Direct Rate Measurements

Figure 2:
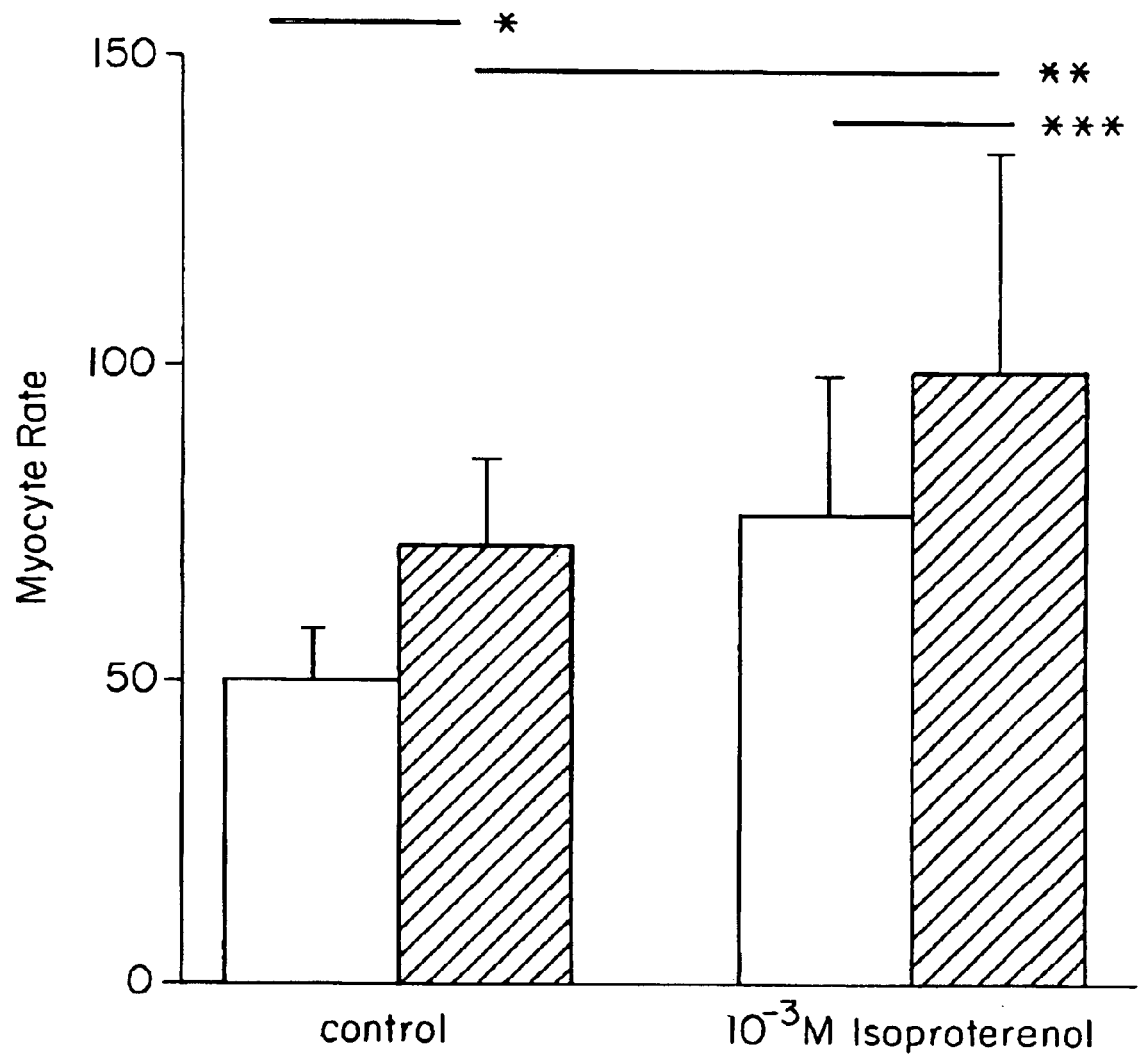
FIG. 2 is a graph showing in vitro murine cardiomyocyte chronotropic rates. The average chronotropic rate of $\beta_2$AR transfected cardiac myocytes (black bars) and control cells (white bars) in the presence and absence (baseline) of $10^{-3}$ M isoproterenol. *$p<0.00001$; $p<0.001$; *$p<0.05$.

The average rate of contraction determined by motion detection was higher in the $\beta_2$AR transfected myocytes, as compared with control transfected cells under both baseline conditions and in the presence of $10^{-3}$ M isoproterenol. FIG. 2 reveals that under control conditions the average rate of contraction of $\beta_2$AR transfected myocytes was significantly higher as compared with control transfected cells (71+/−14 vs. 50+/−10 bpm; p<0.001). The average rate of contraction increased by a similar proportion in both populations with the addition of isoproterenol. In the presence of $10^{-3}$ M isoproterenol, the average rate of contraction of $\beta_2$AR transfected myocytes was significantly higher as compared with the control cells (98+/−26 vs. 75+/−18 bpm; p<0.05).

Example 2
Heart Transplantation and DNA Injection

Neonatal B6D2F1 murine hearts were transplanted into the pinneas of adult mice as previously described (Fulmer, R. et al., *American Journal of Anatomy*, 113:273–286 (1963); Rossi, M. A., *Am J Patho.*, 141(1):183–91 (1992)). Briefly, recipient 6-week-old adult B6D2F1 mice were anesthetized with Avertin 2.5% (vol/vol). After cleaning the dorsum of the pinnea of the mouse ear with 70% ethanol, an incision penetrating only the epidermis, 2–5 mm in length, was made with a scalpel transverse to the longitudinal axis of the ear, 3–4 mm distal to its implantation into the skull. A small pocket between the skin and cartilage was blunt dissected toward the tip of the ear with delicate curved forceps. The total donor neonatal heart was excised without the pericardial sac and inserted into the ear pocket. Gentle pressure with the tips of the forceps was applied to the ear to express air from the pocket and facilitate the adherence between donor and recipient tissues. After 4 to 6 weeks post-transplantation, the transplanted hearts were assayed for visual pulsation and electrocardiographic activity. Visual pulsation of the transplanted tissue was observed in the anesthetized host mice under stereoscopic microscopy. Electrocardiograms (ECGs) of the transplanted hearts were also recorded. Host mice were anesthetized and electrocardiogram limb leads were clipped to the ear surrounding the transplanted heart. ECGs were recorded with a Silogic EC-60 monitor (Silogic Design Limited). Approximately 80% of the transplanted hearts were observed to have visual pulsations and electrocardiographic activity.

Transplanted hearts with both visual pulsations and electrocardiographic activity were then employed in DNA injection experiments. After baseline ECGs were recorded from the transplanted hearts, expression vectors (prepared as described in Example 1) were injected into the atrium of the transplanted hearts similarly as previously described in murine skeletal muscle injection (Wolff, J. A. et al., *Science*, 247 (4949 Pt 1):1465–8 (1990)). Briefly, the $\beta_2AR$ expression vector or the control construct (5 µl DNA (2 µg/ml) in 20% sucrose, 2% Evans Blue, in PBS) were injected into the transplanted hearts with a 33-gauge needle. Electrocardiographic activity was recorded daily for up to 7 days following the injections. The statistical significance of increased heart rates was determined by a Student's t-Test analysis.

Results
Heart Transplant DNA Injections

Figure 3A:
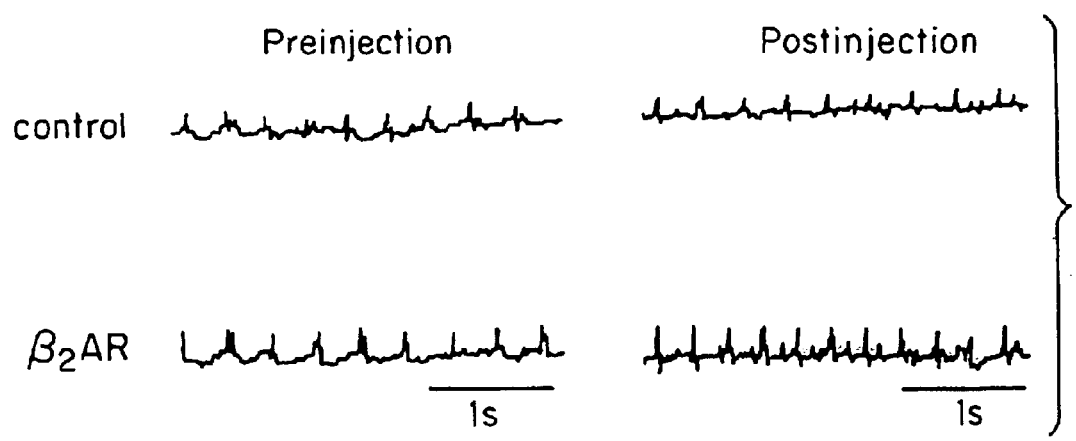
FIG. 3A displays representative ECG tracings recorded from transplanted neonatal murine hearts pre- and two days postinjection with either the $\beta_2$AR construct (n=10) or the control construct (n=10).
Figure 3B:
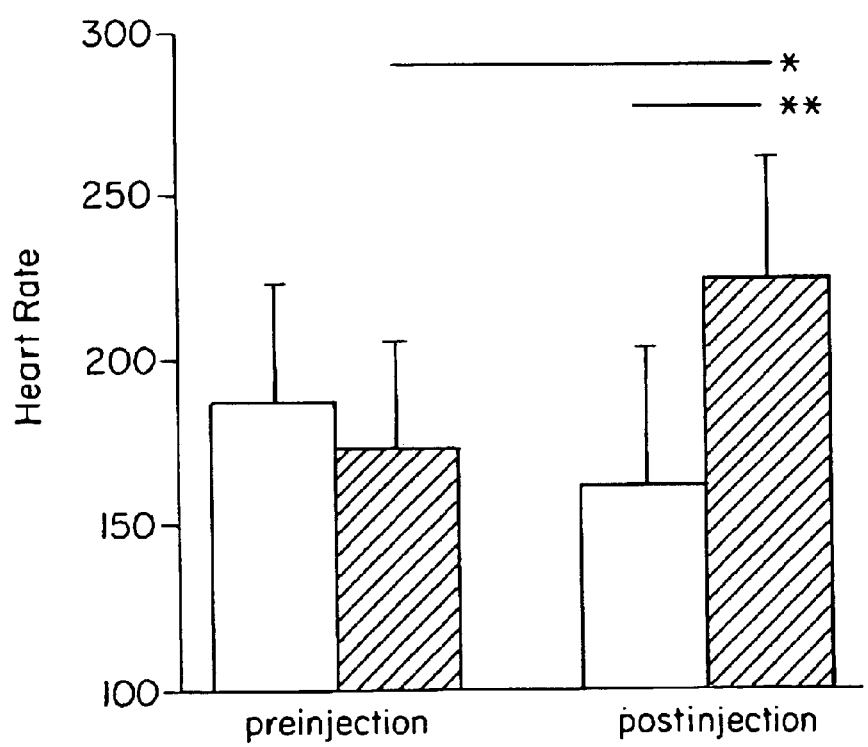
FIG. 3B is a graph displaying the average heart rate of the transplanted hearts pre- and two days postinjection with the $\beta_2$AR construct (white bars) or the control construct (black bars). *$p<0.001$ **$p<0.05$.

Injection of transplanted hearts with the $\beta_2AR$ expression vector, as compared with control constructs generated an increased heart rate. ECGs recorded from the pinnea surrounding the transplanted neonatal hearts demonstrate that $\beta_2AR$ injected hearts exhibit faster cardiac rates, as compared to hearts prior to injection and to hearts injected with control constructs (FIG. 3A). Recordings prior to injection revealed consistent electrocardiographic activity with an average heart rate of 180+/−20 bpm (FIG. 3B). Two days after injection with the $\beta_2AR$ expression vector, the heart rate increased to 220+/−20 bpm, which was significantly higher than the preinjection heart rate (p<0.001) or the heart rate observed with control constructs (D<0.005). The increased heart rate was sustained for 3 to 4 days after which the heart rate returned to baseline levels.

Example 3
Intaracardiac DNA Injection of Endogenous Murine Hearts

The right atria of 6-week-old adult B6D2F1 murine hearts were injected with expression vectors (which were prepared as described in Example 1). Adult mice were anesthetized with avertin 2.5%, and a baseline ECG was recorded. The heart was exposed as previously described (Selge, H. et al., *Angiology*, 11:398–407 (1960); Kitsis, R. N. et al., *Proc Natl Acad Sci USA.*, 88(10):4138–42 (1991)). Briefly, the mice were then intubated and mechanically ventilated with a rodent ventilator (Model 683, Harvard Apparatus, Inc., South Natick, Ma.) with room air. A right anterolateral thoracotomy was then performed and the heart visualized. The $\beta_2AR$ expression vector or the control construct was then introduced into the right atrial wall with a 30-gauge needle, as described above. The lungs were reexpanded and the chest closed in three layers with 4-0 silk sutures. The mice were then allowed to recover spontaneous respiration. Electrocardiographic activity was recorded daily for up to 7 days following the injections. The statistical significance of increased heart rate was determined by a Student's t Test analysis.

$B_2AR$ Immunostaining

Sections of injected hearts were immunostained for the human $\beta_2AR$ as described above. Briefly, $\beta_2AR$ and control expression vector injected transplanted or intact hearts were sectioned to 8-µm sections and fixed with cold acetone for 10 min. The sections were then washed with PBS and blocked with 10% normal serum in PBS for 20 min. Samples were then incubated with rabbit-antihuman $\beta_2AR$ polyclonal antibody (Santa Cruz Biotechnologies) at 1.0 µg/ml as described above. Additionally, sections through the right lateral atrium, the peri-injection site, were scored for the frequency of specific immunostaining in hearts injected with the control and $\beta_2AR$ constructs.

Results
Intercardiac DNA Injections

Figure 4A:
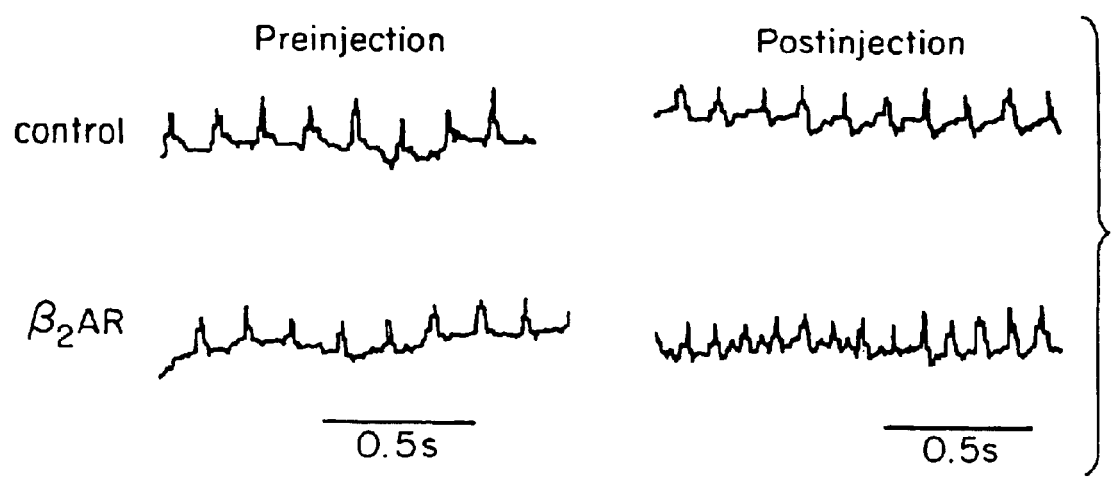
FIG. 4A displays representative ECG tracings of endogenous murine hearts pre- and two days post in vivo injection with either the $\beta_2$AR construct (n=7) or the control construct (n=8).
Figure 4B:
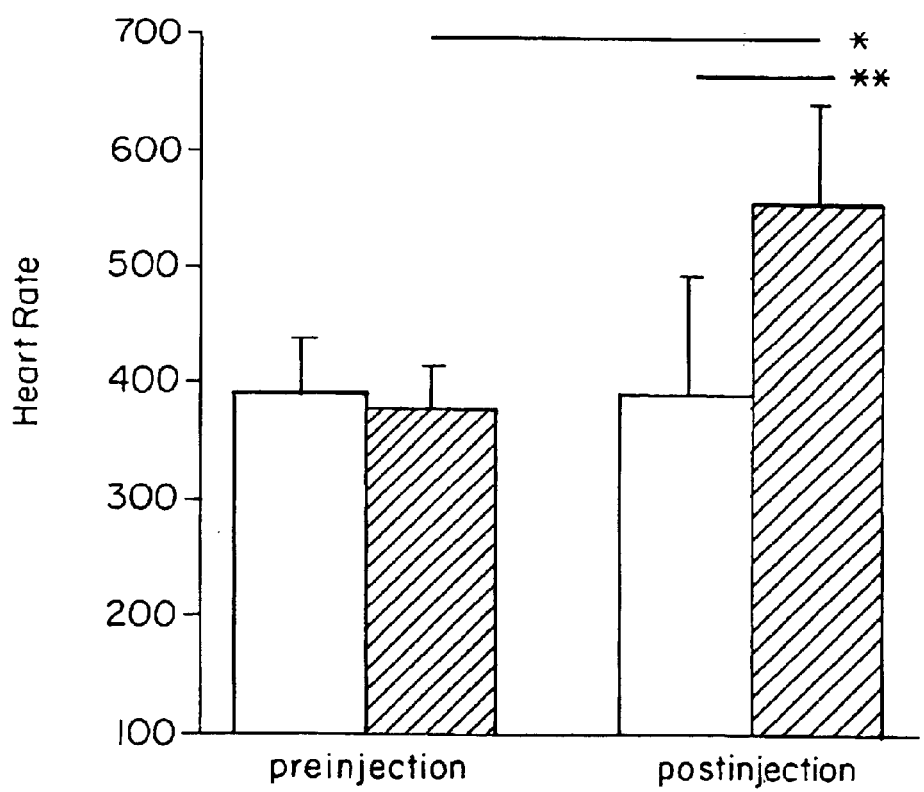
FIG. 4B is a graph displaying the average heart rate of murine hearts pre- and two days post injection with the $\beta_2$AR construct (black bars) or the control construct (white bars). Bar 70 $\mu$m. *$p<0.01$ **$p<0.05$ FIG. 5A are representative surface ECGs recorded 48 hrs after the intracardiac injection of either a control construct (encoding GFP) or a construct encoding $B_2$AR.
Figure 5A:
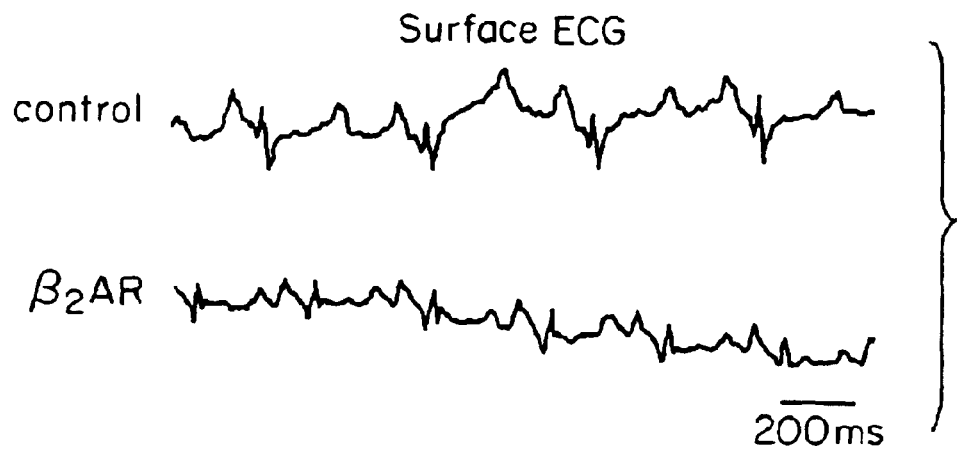
FIG. 5B is a graph summarizing the average cycle lengths pre- and two days post-injection with the control construct (white bars) or the $B_2$AR construct (black bars).
Figure 5B:
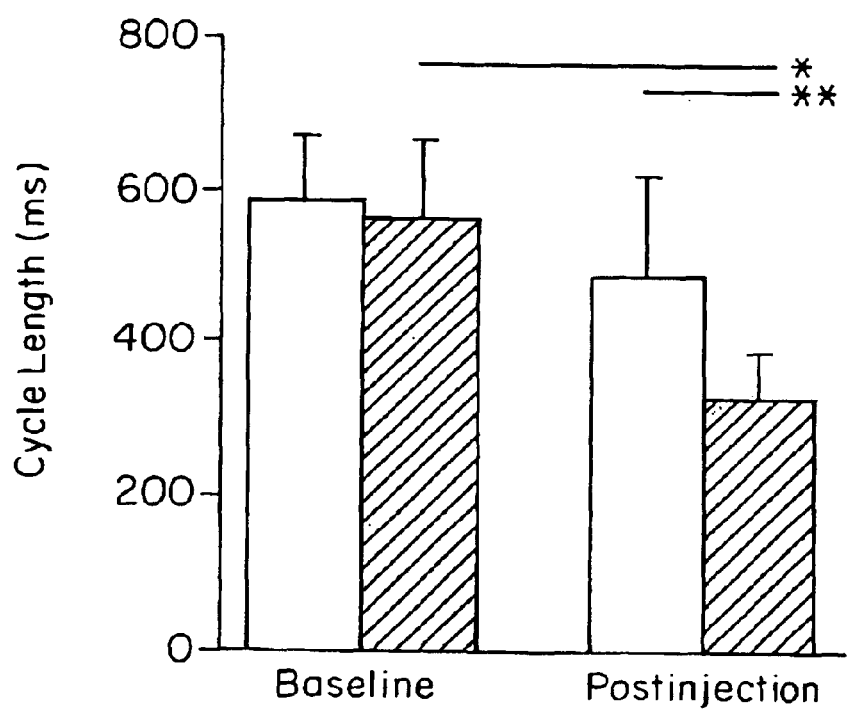

Injection of the $\beta_2AR$ expression vector increased the density of receptor in the right atrium of endogenous hearts. Immunostaining for the human $\beta_2AR$ three days post injection revealed right atrial expression in the hearts injected with the $\beta_2AR$ expression vector, but not in the hearts injected with control construct. Expression of the human $\beta_2AR$ was detected in 81+/−13% of the myocytes in the peri-injection site of the targeted hearts, with no specific staining in the control injected atria. Surface ECGs recorded from adult mice demonstrate that hearts injected with the $\beta_2AR$ expression vector exhibit a higher rate of contraction as compared with hearts prior to injection as well as to the hearts injected with the control construct (FIG. 4A). The average heart rate of the anesthetized adult mice was 370+/−20 bpm prior to injection (FIG. 4B), similar to previously reported rates in resting and anesthetized mice (Milano, C. A. et al., *Science*. 264(5158):582–6 (1994)). Two days after injection with the $\beta_2AR$ expression vector, the heart rate increased to 550+/−42 bpm, which was significantly higher as compared tot he preinjection heart rate (p<0.01), as well as to the control construct postinjection heart rate (p<0.05). The increased heart rate was sustained for 2 to 3 days after which time the heart rate returned to baseline levels.

Example 4
Molecular Enhancement of Porcine Cardiac Chrontropy

The experiment outlined in this example was directed at developing an in vivo gene transfer technique to identify and study genes that can be employed to selectively upregulate heart rate and alter cardiac rhythm in the intact heart in a large animal model. The Yorkshire pig was chosen for its anatomic and physiologic similarity to the human cardiovascular system, and because porcine models have been successfully employed in other gene therapy studies involving cardiac vasculature. Constructs encoding either the human b₂ adrenergic receptor (β₂AR) or green fluorescent protein were injected into the right atrium of native Yorkshire pig hearts. Percutaneous electrophysiologic recording catheters equipped with 33 g circular injection needle were positioned in the mid-lateral right atrium. At the site of the earliest atrial potential the circular injection needle was rotated into the myocardium, and the β₂AR (n=6) or control plasmid constructs (n=5) injected. The average atrial electrocardiogram to surface P wave interval at the injection site was similar in pigs injected with the β₂AR and control constructs (14+/−10 vs. 12+/−10 ms). The average PR interval and P wave axis were similar in the β₂AR- and control-animals, both at baseline and 48 hr post injection. Injection of the β₂AR construct significantly enhanced chronotropy, as compared to control injections. The average cycle length of the pig heart rate was 567+/−100 ms prior to injection. Two days after injection with plasmid encoding the β₂AR the cycle length decreased to 327+/−60 ms, which was significantly faster as compared to the control cycle length 488+/−130 ms ($p<0.03$).

Plasmid Constructs cDNA encoding the human β₂AR was the kind gift of Dr. Robert J. Lefkowitz (Duke University Medical Center, Durham N.C.). A 2.25 kb Sal 1-BamH 1 fragment, the human β₂AR SV40 cDNA was ligated into a Sal 1-BamH 1 site 3' to the (β actin promoter) (βAP) in a pBR322 vector to generate pBR322-βAP-β₂AR-SV40. The plasmid construct encoding the humanized green fluorescent protein (GFP) with a CMV promoter element was purchased from Clontech, and served as a control vector. The injection vehicle was PBS with 20% sucrose and 2% Evans blue.

Injection Catheter

Electrophysiology recording catheters were custom designed and manufactured by Medtronic, Inc. The polyurethane-coated catheter was 7F in size and was supported with an 8F sheath. The distal end of the catheter was terminated with a 3½ turn 33 gauge corkscrew shaped needle allowing it to impale securely onto tissues to record local intracardiac electrograms. The proximal end of the catheter was terminated with a lure lock injection port allowing it to accept standard sized syringes. The total unit had 70 µL of dead space).

Electrophysiologically-Guided Intracardiac Injection

Female Yorkshire pigs weighing 15–20 kg were initially anesthetized with intramuscular ketamine (10(g/Kg) and intubated. The animals were then given 2% isoflurane, and ventilated with a large animal ventilator (Hallowell model 2000). Heart rate, blood pressure and arterial oxygen saturation were monitored during the duration of the procedure. By sterile technique, the right femoral vein was exposed, cannulated, and an 8F sheath inserted. Under fluoroscopic guidance the 8F electrophysiologic injection catheter was introduced and advanced to the right atrium. Simultaneous 6 lead surface and intracardiac electrocardiograms were recorded with a multichannel recorder (EVR PPG Biomedical). The A-P interval (ms), cycle length (ms), PR interval (ms), and P wave axis (°) were measured. At the site of earliest A wave the injection needle was rotated 270° into the atrial myocardium. The recombinant DNA constructs (200(L; 100 (g/mL), GFP alone (n=5) or β₂AR/GFP (5:1 M/M) samples (n=6), were then injected into the atrial myocardium. The catheter was then disengaged and removed from the animal. The animal was observed from an additional 10 min and monitored for complications. The vascular sheath was then removed, the vein sutured, and the incision site closed. Anesthesia was then discontinued. After regaining spontaneous respirations that animals were placed in individual pens. The animals were monitored on an hourly basis for the next three hours, and then daily until the termination of the experiments, 96 hr post injection.

Serial Surface Electrocardiogram Recordings and Analysis

Serial surface electrocardiogram were recorded daily on all animals during the duration of the study. The pigs were anesthetized with ketamine as above. Simultaneous 6 lead surface electrocardiograms were recorded. The cycle length, PR interval, and P wave axis were measured. Statistical significance was determined by a Student's t-Test analysis.

β₂AR Immunostaining

At the termination of the experiments the animals were sacrificed and the hearts explanted. The injection sites were harvested for sectioning and immunostaining. b₂AR and control expression vector injected atria were sectioned to 10 mm sections and fixed with cold methanol for 10 min. The sections were then washed with PBS and blocked with 10% normal serum in PBS for 20 min. Samples were then incubated with rabbit-anti-human b₂AR polyclonal antibody (Santa Cruz Biotechnologies) at 1.0 mg/mL for 1 hr. Samples were then incubated with the primary antibody at 1.0 mg/mL in PBS with 1% bovine serum albumin for one hr in a humid chamber at 25° C. The sample was then washed with PBS three times and then incubated with the secondary donkey-anti-rabbit Cy3 polyclonal antibody (Jackson ImmunoResearch) at a 1:1000 dilution in PBS with 1% bovine serum albumin for one hr in a humid chamber at room temperature. The samples were washed with PBS three times and mounted with 90% glycerol in PBS. GFP expression was identified by employing epifluorescence filters for green fluorescence$_{(excitation\ 405\ nm/emission\ 490\ nm)}$. Immunostaining for the human β₂AR was identified by employing epifluorescence filters for red fluorescence (excitation 488 nm/emission 540 nm).

Results

Electrophysiologically-Guided Intercardiac cDNA Injections

The animals were anesthetized, intubated, and venous access obtained as described above. The injection catheter was advanced to the right lateral atrium under fluoroscopic guidance. Simultaneous surface and intracardiac electrocardiograms were recorded. The catheter was positioned at the site of the earliest atrial activity. The atrial potential at the injection sight was similar in both the pigs injected with the control (14+/−10 ms) and the b₂AR encoding constructs (12+/−10 ms). In addition, both the average PR interval and P wave axis on the surface ECG was similar for both groups prior to injection, Table 1. All the animals tolerated the procedure well.

Post Injection ECG Analysis

Serial surface ECGs recorded from the pigs after construct injection demonstrate that the average PR interval and P wave axis on the surface ECG was similar to the measurements prior to injection, Table 1.

TABLE 1

Electrocardiographic Measurements

| | Baseline | | 48 hr post | |
| --- | --- | --- | --- | --- |
| | Control | β₂AR | Control | β₂AR |
| P wave axis (°) | 65 +/− 7 | 56 +/− 20 | 60 +/− 20 | 62 +/− 15 |
| PR (ms) | 85 +/− 10 | 92 +/− 9 | 86 +/− 8 | 86 +/− 9 |

The heart rate increased in the hearts injected with the β₂AR plasmid as compared to the control cycle lengths, FIG. 2A. The cycle length of the pigs was 567+/−100 ms prior to injection. Two days after injection with plasmid encoding the $\beta_2$AR the cycle length decreased to 327+/−60 ms, which was significantly faster as compared to the control cycle length 488+/−130 ms (p<0.03), FIG. 2B. The difference in cycle length after control injection was not statistically significant (p>0.3). These changes correlated with a 49% increase in the average heart rate in the $\beta_2$AR injected pigs (183+/−28 vs. 122+/−25 bpm). The increased heart rate was sustained for 1 to 2 days after which the heart rate trended to baseline levels. All animals survived until the termination of the experiment. In summary, these studies demonstrate that the basal rate of the heart can be enhanced by local delivery of exogenous genes. The present example demonstrates that local targeting of gene expression may be a feasible modality to regulate the cardiac pacemaking activity. In addition, the porcine model system also provide an experimental basis for developing future human clinical gene transfer protocols designed to upregulate heart rate and alter cardiac rhythm.

Post Injection Immunostaining

Injection of the cDNA constructs lead to the expression of the encoded genes. Sections of the right atrial tissue at the site of injection revealed the presence of GFP. Immunostaining of the sections revealed a colocalization of the human $\beta_2$AR in the co-injected with the $\beta_2$AR-encoding constructs.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of transiently upregulating heart rate in a mammal by introducing at least one fetal or embryonic cardiomyocyte transfected or transduced with at least one gene that upregulates heart rate, said gene selected from the group consisting of: $\beta_2$AR, $\beta_1$AR, and $G_{\alpha s}$, wherein expression of the at least one gene in the transduced cardiomyocytes results in transiently upregulating heart rate in said mammal.

2. A method of upregulating heart rate in a mammal by introducing a construct comprising at least one gene selected from the group consisting of $\beta_2$AR, $\beta_1$AR, and $G_{\alpha s}$, wherein the at least one gene is operably linked to a promoter, and wherein said construct is suitable for localized stable gene expression in mammalian cardiac atrial tissue, and wherein said construct is introduced by direct myocardial injection or direct endocardiac transfection or transduction, and expression of said construct results in upregulating heart rate in the mammal.

3. The method of claim 2, wherein the promoter comprises an inducible promoter.

4. The method of claim 2, wherein the construct is introduced into the sinoatrial node region of a mammalian heart.

5. The method of claim 2, wherein the method further comprises in vivo administration of an adrenergic agonist.

6. The method of claim 5, wherein the adrenergic agonist is isoproterenol.

* * * * *